United States Patent [19]
Kawaguchi et al.

[11] Patent Number: 6,007,527
[45] Date of Patent: *Dec. 28, 1999

[54] DISPOSABLE DIAPER WITH A MECHANICAL FASTENER AND AN ADHESIVE TAB FOR DISPOSING OF THE DIAPER

[75] Inventors: Haruko Kawaguchi; Megumi Kato; Harumitsu Toyoda; Taiki Uchiyama, all of Tochigi-ken, Japan

[73] Assignee: Kao Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/758,778

[22] Filed: Dec. 3, 1996

[30] Foreign Application Priority Data

| Dec. 4, 1995 | [JP] | Japan | 7-315680 |
| Apr. 17, 1996 | [JP] | Japan | 8-095693 |
| May 21, 1996 | [JP] | Japan | 8-125510 |

[51] Int. Cl.$^6$ .................................................. A61F 13/15
[52] U.S. Cl. .......................... 604/386; 604/391; 604/389; 428/343; 156/315
[58] Field of Search ................... 64/385.1, 386, 64/387, 389–391; 428/343; 156/315, 227

[56] References Cited

U.S. PATENT DOCUMENTS

| 4,209,016 | 6/1980 | Schaar | 604/390 |
| 4,869,724 | 9/1989 | Scripps | 604/389 |
| 4,963,140 | 10/1990 | Robertson et al. | 604/391 |
| 5,019,065 | 5/1991 | Scripps | 604/391 |
| 5,053,028 | 10/1991 | Zoia et al. | 604/389 |
| 5,108,384 | 4/1992 | Goulait | 604/390 |
| 5,201,727 | 4/1993 | Nakanishi et al. | 604/390 |
| 5,282,914 | 2/1994 | Spendlove | 156/227 |
| 5,660,659 | 8/1997 | Caldwell | 156/227 |

FOREIGN PATENT DOCUMENTS

| 2257895 | 1/1993 | European Pat. Off. | 604/385.1 |
| 529681 | 3/1993 | European Pat. Off. | |
| 24372 | of 1990 | Japan. | |
| 24373 | of 1990 | Japan. | |

Primary Examiner—Mark O. Polutta
Attorney, Agent, or Firm—Birch, Stewart, Kolasch & Birch, LLP

[57] ABSTRACT

A disposable diaper including a liquid permeable topsheet, a liquid impermeable backsheet, and an absorbent member interposed therebetween, the disposable diaper being provided with a front waist body portion which is located on the stomach side of a diaper wearer when the wearer puts on the diaper and a rear waist body portion which is located on the back side of the wearer, the rear waist body portion being provided with tape tabs connected at opposite lateral sides thereof, respectively, each of the tape tabs being provided with a projection member or a recess member of a mechanical fastener, the front waist body portion being provided with a counterpart portion on the backsheet side for allowing the projection member or the recess member to be engaged with or be retained by the counterpart portion;

each of the tape tabs including an adhesive portion which is formed by applying an adhesive agent thereto;

the adhesive portion being provided on the surface side of the tape tab opposite to where the projection member or the recess member of the mechanical fastener is provided; and said tape tabs being configured in such a manner that, when the disposable diaper is formed into a shape for disposal where the diaper is rolled up with the backsheet side facing outwardly, the tape tabs maintain the disposal shape of the diaper by means of at least the adhesive portions attached to the liquid permeable backsheet.

8 Claims, 7 Drawing Sheets

DISPOSABLE DIAPER WITH A MECHANICAL FASTENER AND AN ADHESIVE TAB FOR DISPOSING OF THE DIAPER

BACKGROUND OF THE INVENTION

1. Field of the Invention

This invention relates to a disposable diaper in which tape tabs are continuously connected respectively to opposite lateral side portions of a rear waist body portion. Each tape tab is provided with a projection member or a recess member of a mechanical fastener, and a counterpart portion for retaining the projection member or recess member of the mechanical fastener. The counterpart portion is provided on the stomach side. More particularly, this invention relates to a disposable diaper having a fastener in which the rear waist body portion can positively be attached to or retained by the stomach side without peeling paper, and in a disposable form where the form or shape of the diaper ready to be disposed can be easily and positively maintained.

2. Description of the Related Art

A disposable diaper has been known which comprises a liquid permeable topsheet, a liquid impermeable backsheet, and an absorbent member interposed therebetween. It has a front waist body portion which is located on the stomach side and a rear waist body portion which is located on the back side of the diaper wearer. During use, the opposite side areas of the rear waist body portion are retentively attached to the stomach side by a mechanical fastener. In such a disposable diaper, a projection member or a recess member of the mechanical fastener is provided on each tape tab which is connected with each of the opposite lateral side areas of the rear waist body portion. A counterpart portion is provided on the stomach side and adapted to retentively engage the projection member or recess member of the mechanical fastener.

Compared to a diaper in which the rear waist body portion is retentively attached to the stomach side by an adhesive fastener, a disposable diaper of the above-mentioned type has such advantages that: degradation of a retentive attaching force caused by contamination due to powder or the like is less likely to occur. Accordingly, there is no fear that the front waist body portion does not become easily separated from the rear waist body portion when the former is to be peeled off the latter, preventing breakage of the backsheet of the front waist body portion. When peeling the mechanical fastener, the rear waist body portion can easily be peeled off the front waist body portion and reducing the possibility of tearing of the backsheet at the front waist body portion.

However, in such a conventional disposable diaper, it is difficult to retentively attach the tape tabs to other areas than the counterpart portion. Accordingly, a disposable form of the conventional diaper, which is formed by rolling up the disposable diaper so that the absorbed liquid or the like will not leak inwardly, is difficult to maintain when the conventional disposable diaper is to be disposed.

In order to obviate the above inconveniences, there is proposed a technique, as discussed in Japanese Patent Application Laid-Open Nos. 4372/1990 and 4373/1990, in which each tape tab is provided with both a mechanical fastener portion functioning as a mechanical fastener and an adhesive portion functioning as an adhesive fastener.

Specifically, in Japanese Patent Application Laid-Open No. 4372/1990, as shown in the attached FIG. 12A, the tape tabs 713 are further allowed to extend beyond the mechanical fastener portions 713a. An adhesive agent is applied to the same surface as the mechanical fastener portions 713a to form adhesive portions 713b. The adhesive portions 713b are placed one upon the other in a superimposed relation, which is further folded upon the mechanical fastener portions 713a, or as shown in the attached FIG. 13, each tape tab 813 is provided only with an adhesive portion 813b, and a mechanical fastener piece 813a is peelably attached to this adhesive portion 813b. Also, in the Japanese Patent Application Laid-Open No. 4373/1990, as shown in the attached FIG. 14, one surface of each tape tab 913 is provided with a mechanical fastener portion 913a and with an adhesive portion 913b so that both the mechanical fastener portion 913a and the adhesive portion 913b are retentively attached to the stomach side when the diaper is put on the diaper wearer.

As shown in the attached FIG. 12A, with respect to the technique in which the tape tabs 713 are further allowed to extend beyond the mechanical fastener portions 713a to form the adhesive portions 713b, for disposing the disposable diaper, as shown in the attached FIG. 12 B, each tape tab 713 is developed to allow the adhesive portion 713b to be exposed. This adhesive portion 713b is attached to the backsheet (not shown) which is located outwardly in the disposable form, thus enabling to maintain the disposable form. However, in the disposable form, since the area provided with the mechanical fastener portion 713a is arranged on the backsheet side and is not firmly secured to the backsheet (not shown), the tape tabs 713 are difficult to retain on the backsheet (not shown) and the disposable form is difficult to be maintained in its favorable condition.

On the other hand, with respect to the technique of the attached FIG. 13, in which the mechanical fastener piece 813a is peelably attached to the adhesive portion 813b, the adhesive portion 813b can be exposed by peeling off the mechanical fastener piece 813a and the disposable form can be maintained by this adhesive portion 813b when the disposable diaper is to be disposed of. However, it still involves another problem in that much time and labor is required to dispose the mechanical fastener piece 813a.

Furthermore, as shown in the attached FIG. 14, with respect to the technique in which both the mechanical fastener portion 913a and the adhesive portion 913b are provided on one surface of each tape tab 913, the disposable form can be maintained by attaching the adhesive portion 913a directly to the corresponding tape tab and the backsheet (not shown) when the disposable diaper is to be disposed. However, since the adhesive portion is used when the diaper is worn, there remains the aforementioned problems inherent in the prior art, in which the retentive attaching force is degraded by contamination due to powder or the like and the front waist body portion does not easily separate from the rear waist body portion when the former is to be peeled off the latter. This results in breakage of the backsheet of the front waist body portion. When this occurs, reengagement of the stomach side with the back side is very difficult to perform.

SUMMARY OF THE INVENTION

It is, therefore, an object of the present invention to provide a disposable diaper in which the rear waist body portion can positively be attached to and retained by the stomach side, and where there is no need for a peeling paper while in a disposable form, the diaper can be easily and securely maintained.

The present invention has achieved the above object by providing a disposable diaper including a liquid permeable topsheet; a liquid impermeable back-sheet; and an absorbent member interposed therebetween, the disposable diaper being provided with a front waist body portion which is located on the stomach side of a diaper wearer when the wearer puts on the diaper and a rear waist body portion which is located on the back side of the wearer; the rear waist body portion being provided with tape tabs connected at opposite lateral sides thereof, respectively; each of the tape tabs being provided with a projection member or a recess member of a mechanical fastener to thereby form an engaging portion; the front waist body portion being provided with a counterpart portion on the backsheet side for allowing the projection member or the recess member to be engaged with or be retained by the counterpart portion; each of the tape tabs including an adhesive portion which is formed by applying an adhesive agent thereto; the adhesive portion being provided on the surface side of the tape tab opposite where the projection member or the recess member of the mechanical fastener is provided; and the tape tabs being configured in such a manner that, when the disposable diaper is formed into a disposal shape in which the diaper is rolled up with the backsheet side facing outside, the tape tabs maintain the disposal shape of the diaper by means of at least the adhesive portions attached to the backsheet.

Advantageously, the projection member or the recess member of the mechanical fastener is provided on the backsheet side of each of the tape tabs. Each of the tape tabs is provided, with an adhesive portion at an area in the vicinity of a free end portion of the surface of the tape tab which is located on the side opposite the surface where the projection member or the recess member of the mechanical fastener is provided. Each of the tape tabs is provided, on the same surface thereof where the adhesive portion is disposed but where the adhesive portion does not exist, with an associated portion capable of peelably attaching the adhesive portion thereto without losing adhesive properties of the adhesive agent. Each of the tape tabs is bent back such that the adhesive portion and the associated portion are attached together, and such that the projection member and the recess member are arranged on a topsheet side.

Also, the projection member or the recess member of the mechanical fastener is provided on the backsheet side of each of the tape tabs. The adhesive portion is provided on the surface of the tape tab which is located on the side opposite the projection member or the recess member of the mechanical fastener. An associated portion is provided on the topsheet side on the opposite lateral sides of the rear waist body portion while the tape tabs are bent back at areas in the vicinity of side edges of the rear waist body portion such the adhesive portion of the tape tab is attached to the associated portion of the rear waist body portion. The projection member or the recess member of the mechanical fastener is arranged on the topsheet side.

Also, each of the tape tabs comprise a retaining tape portion having the projection member or the recess member of the mechanical fastener; an adhesive tape portion having adhesive portion; the retaining tape portions are connected to the opposite lateral side portions of the rear waist body portion, respectively; a surface of the topsheet side of the retaining tape portion being provided with the projection member or the recess member of the mechanical fastener; a surface of the backsheet side of the retaining tape portion being provided with the associated portion; and the adhesive portion of the adhesive tape portion is attached to the associated portion.

Also, the tape tabs each comprise a retaining tape portion having the projection member or the recess member of the mechanical fastener; an adhesive tape portion having the adhesive portion; the retaining tape portions are connected to the opposite lateral side portions of the rear waist body portion, respectively; the projection member or the recess member of the mechanical fastener is provided on the topsheet side of the retaining tape portion; the adhesive tape portion is connected with a distal end portion of the retaining tape portion; the adhesive portion provided on the adhesive tape portion is located on the opposite surface side with respect to that surface of the retaining tape portion where the projection member or the recess member of mechanical fastener is provided; the retaining tape portion is provided, on the back side of that surface where the projection member or the recess member of the mechanical fastener is disposed, with the associated portion; and a connecting portion between the adhesive tape portion and the retaining tape portion is bent, and the adhesive portion is attached to the associated portion.

According to a disposable diaper of the present invention, the rear waist body portion can positively be attached to and retained by the front waist body portion, there is no need for providing a peeling paper, and a disposable form of the diaper can be easily and positively formed.

BRIEF DESCRIPTION OF THE DRAWINGS

FIG. 2B is a side view showing a form of use of the tape tab prior to when the disposable diaper of FIG. 1 is to be disposed of;

FIG. 4B is a front view showing a form of use of the tape tab prior to when the disposable diaper according to the second embodiment of the present invention is to be disposed of;

FIG. 4D is a side view showing a form of use of the tape tab prior to when the disposable diaper according to the second embodiment of the present invention is to be disposed of;

FIG. 6B is a side view showing a form of use of the tape tab prior to when the disposable diaper of FIG. 5 is to be disposed of;

FIG. 8B is a side view showing a form of use of the tape tab prior to when the disposable diaper of FIG. 7 is to be disposed of;

FIG. 9B is a side view showing a form of use of the tape tab prior to when the disposable diaper ac-cording to the fifth embodiment of the present invention is to be disposed of;

Fig. 11B is a side view showing a form of use of the tape tab prior to when the disposable diaper of FIG. 10 is to be disposed of;

FIG. 12B is a side view showing a form of use of the tape tab of FIG. 12A prior to when the disposable diaper is to be disposed of;

DETAILED DESCRIPTION OF THE INVENTION

One embodiment of a disposable diaper according to the present invention will now be described with reference to the accompanying drawings.

Figure 1:
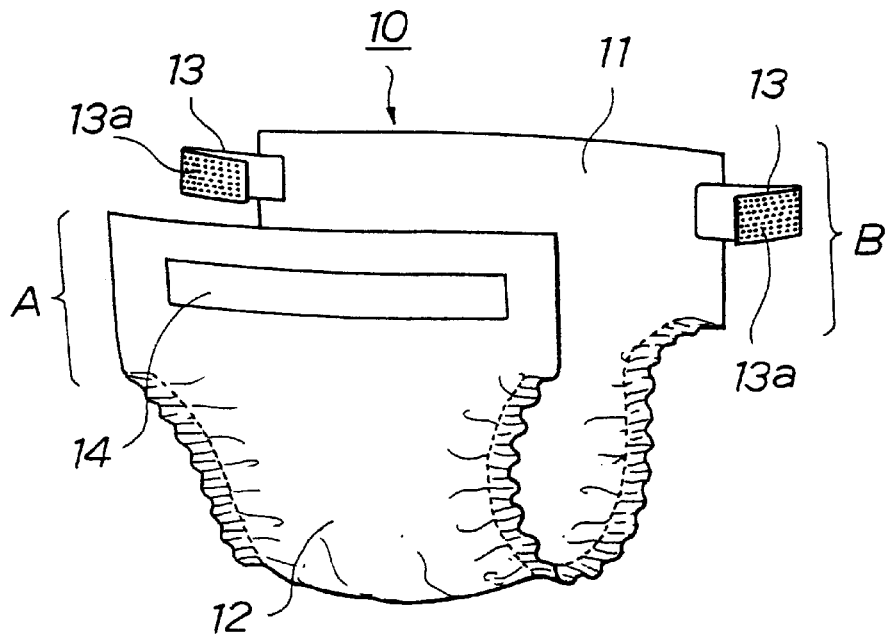
FIG. 1 is a perspective view showing a disposable diaper according to the first embodiment of the present invention.
Figure 2A:
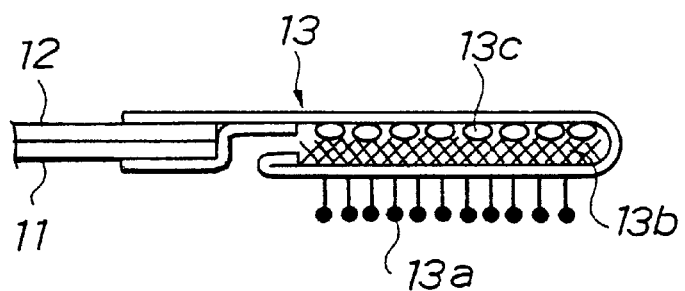
FIG. 2A is a side view showing a tape tab of the disposable diaper of FIG. 1.
Figure 2B:
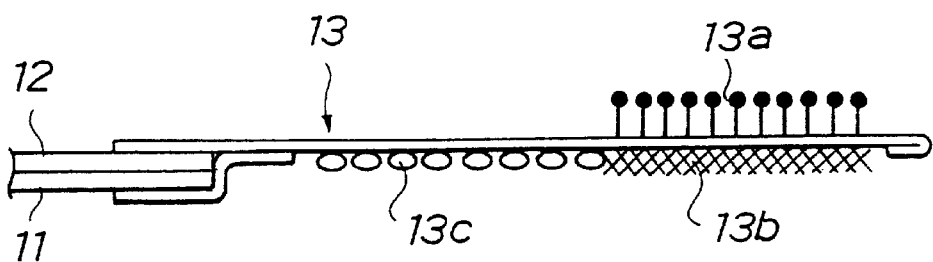
Figure 3:
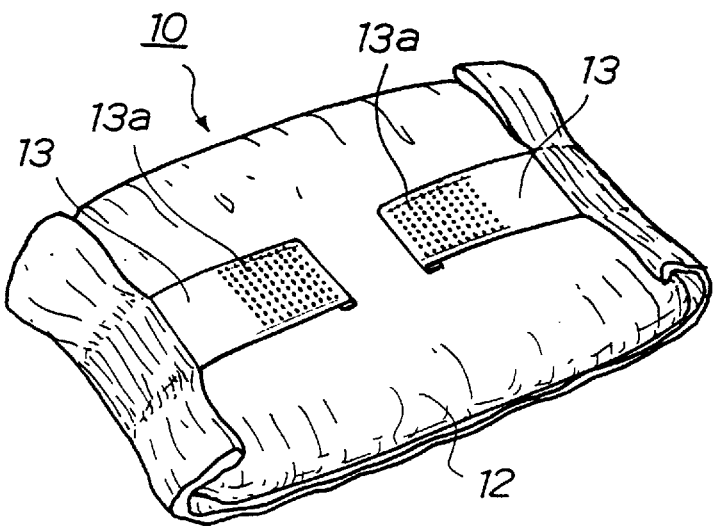
FIG. 3 is a perspective view showing the disposable diaper of FIG. 1 in a disposal form.

FIG. 1 is a perspective view showing a disposable diaper according to the first embodiment of the present invention, FIG. 2A is a side view showing a tape tab of the disposable diaper of FIG. 1, FIG. 2B is a side view showing a form of use of the tape tab when the disposable diaper of FIG. 1 is disposed, and FIG. 3 is a perspective view showing a form of use when the disposable diaper of FIG. 1 is disposed.

As shown in FIG. 1, a disposable diaper 10 of this embodiment includes a liquid permeable topsheet 11, a liquid impermeable backsheet 12, and an absorbent member (not seen) interposed therebetween. The disposable diaper 10 is provided with a front waist body portion A which is located on the stomach side and a rear waist body portion B which is located on the back side of the diaper wearer when the diaper wearer puts on the diaper 10. The rear waist body portion E) is provided at opposite lateral sides thereof with tape tabs 13. The tape tabs 13 are connected respectively with the lateral sides of the rear waist body portion B. Each of the tape tabs 13 is provided with projection members 13a of a mechanical fastener to thereby form an engaging portion. The stomach side A is pro-vided with a counterpart portion 14 for retaining the projection members 13a of the mechanical fastener. Constructions thereof are known per se.

In the disposable diaper 10 of this embodiment, as shown in FIGS. 2A and 2B, the tape tab 13 is provided with an adhesive portion 13b which is formed by applying an adhesive agent, and on an opposite surface side of that surface of the tape tab 13, the projection member 13a of the mechanical fastener is provided.

This embodiment will now be described in de-tail. The projection members 13a of the mechanical fastener are provided on the backsheet 12 side of the tape tab 13, and the adhesive portion 13b is provided on the opposite side of the tape tab 13 at an area in the vicinity of a free end portion of the tape tab 13. An associated portion 13c is provided on the same surface thereof where adhesive portion 13b is disposed but at the area of the surface where the adhesive portion 13b does not exist. The associated portion 13c is designed such that the adhesive portion 13b can peel-ably be attached to the associated portion 13c without losing the adhesive properties of the adhesive agent. As shown in FIG. 2A, the tape tab 13 is bent such that the adhesive portion 13b is attached to the associated portion 13c, and the projection members 13a are arranged on the topsheet 11 side.

The embodiment of FIG. 1 will now be described in more detail. One end of each tape tab 13 is attached to the opposite lateral sides of the rear waist body portion B. The projection members 13a of a mechanical fastener are secured to about half areas of the free ends of extended portions of the tape tabs 13, with the half areas being on the surface of the tape tabs 13 which are located on the backsheet 12 side. The counterparts 13c are provided on the remaining half areas on the opposite surfaces of the tape tabs 13 by applying a peeling treatment thereto. The adhesive portion 13b is formed by applying an adhesive agent to about a half portion on the free end side on the side opposite the projection members 13a.

The disposable diaper 10 according to this embodiment has a recess member of a mechanical fastener to engage the projection members 13a. This recess member is formed on the front waist body portion A of the disposable diaper 10 and defines the counterpart portion 14.

As the projection member 13a of the mechanical fastener, a projection member of MAGIC TAPE (registered trademark, manufactured by KURARAY CO., LTD.), a projection member of a QUICKRON (registered trademark, manufactured by YKK), a projection member of a MAGI-CLOTH (registered trademark, manufactured by KANEBO CO., LTD.) and the like, which are conventionally used as tape tabs, can be employed without any particular limitation.

As the recess member of the mechanical fastener forming the counterpart 14, a recess member of MAGIC TAPE (registered trademark, manufactured by KURARAY CO., LTD.), a recess member of QUICKRON (registered trademark, manufactured by YKK), a recess member of MAGICLOTH (registered trademark, manufactured by KANEBO CO., LTD.), tricot knit fabric and the like, which are capable of engagement with the projection member 13a of the mechanical fastener, can be employed without any particular limitation.

The peeling treatment for forming the associated portion 13c can be performed by coating or spraying a peeling agent to the surface of each tape tab 13 or securing a peelable tape having a peeling agent or by other means.

The above-mentioned peeling agent or the peeling agent of the peelable tape is capable of peelably attaching the adhesive portion 13b without losing the adhesive properties of the adhesive agent on adhesive portion 13b. In this embodiment, the peeling agent particularly also serves as an adhesive agent also after the adhesive portion 13b is peeled off. The peeling agent or the peeling agent component of the peelable tape may preferably be selected from the group consisting of silicone resins, fluorine resins, octadecyl iso-cyanate or the like. The associated portion 13c is particularly preferably formed by applying the silicone resins to the tape tab 13 and then dried by heating or the like.

The adhesive portions 13b can be formed by applying an adhesive agent to the tape tabs 13 or by securing a tape having an adhesive agent, or by other means.

The material of the adhesive agent may be selected from rubber adhesive agents, silicone-contained rubber adhesive agents, acrylic adhesive agents, silicone-contained acrylic adhesive agents, silicone adhesive agents or the like. Examples of the rubber adhesive agents include those of natural rubbers, styrene-butadiene, polyisobutylene or the like. Examples of the silicone-contained rubber adhesive agents include those obtained by adding or applying silicone to the rubber adhesive agents. Examples of the acrylic adhesive agents include the ordinary adhesive agents chiefly composed of acrylic polymer. Examples of the silicone-contained acrylic adhesive agents include those obtained by adding or applying silicone to the acrylic adhesive agents. Examples of the silicone adhesive agents include the ordinary adhesive agents chiefly composed of silicone rubber.

The peeling force between the adhesive portion 13b and the associated portion 13c is preferably from 25 to 500 g/25 mm width particularly about 100 g/25 mm. If the peeling force is smaller than 25 g/25 mm, there is a fear that the adhesive portion 13b and the associated portion 13c are peeled off in wear. If the peeling force is larger than 500 g/25 mm, the adhesive portion 13b is not readily peeled off in use.

It should be noted that this peeling force between the adhesive portion 13b and the associated portion 13c is determined by a load obtained by per-forming a peeling test of 180 degrees with respect to the adhesive portion 13b and the associated portion 13c of the tape tab 13 which are attached together at an area of the width of 25 mm, then pressed hard together by a roller of 1 kg rolling on it for a full forward and backward distance, then stored for 24 hours at 40° C. and 80% RH, and then left as it is at a room temperature for 30 minutes, by a tension universal tensile testing instrument under the circumstances of 20° C. and 65% RH with an inter-chuck distance of 50 mm, and at a tensile speed of 300 mm/min.

The disposable diaper 10 thus constructed according to this embodiment is used by allowing the projection members 13a to be retained by recess members in the counterpart portion 14.

For disposing the disposable diaper 10, as shown in FIG. 2B, the end of the tape tab 13 is pulled to peel the adhesive portion 13b off the associated portion 13c so that the adhesive portion 13b and the associated portion 13c are exposed on the backsheet 12 side. Then, the disposable diaper 10 is rolled up with the backsheet 12 side facing outwardly and in that state, the adhesive portion 13b and the associated portion 13c are exposed the backsheet 12. As a consequence a form of the disposable diaper 10 ready to be disposed as shown in FIG. 3 can be obtained and secured.

In this way, according to the disposable diaper 10 of this embodiment, in the state that the tape tabs 13 are folded over and the adhesive portions 13b and the counterparts 13c are attached together, the projection members 13a are arranged on the topsheet 11 side and serve as retaining tapes for retaining the disposable diaper on the wearer.

According to the disposable diaper 10 of this embodiment, since each adhesive portion 13b is covered with the associated portion 13c and not used when the disposable diaper 10 is worn by the diaper wearer, the adhesive is not weakened when the diaper is in use, and the advantageous features of the mechanical fastener can fully be exhibited.

Further, according to the disposable diaper 10 of this embodiment, since each adhesive portion 13b is covered with the associated portion 13c formed on the tape tab 13, peelable sheets, which would otherwise be required to be disposed of when the adhesive portion 13b is exposed, are not required when the disposable diaper 10 is disposed of.

Moreover, according to the disposable diaper 10 of this embodiment in particular, since the associated portion 13b is adhesive and attached to the backsheet of the diaper in the form of disposal, the disposal form of the diaper can more easily and positively be maintained.

Also, according to the disposable diaper 10 of this embodiment, almost all the area of the surface of the tape tab 13 on the topsheet side is adhesive and attached to the backsheet of the diaper in the form of disposal. Accordingly, the disposal form of the diaper can more easily and positively be maintained.

The second embodiment of a disposable diaper according to the present invention will now be described. In this second embodiment, the same component members as the disposable diaper 10 of the first embodiment of FIGS. 1 through 3 are denoted by the same reference numerals and description thereof is omitted.

Figure 4A:
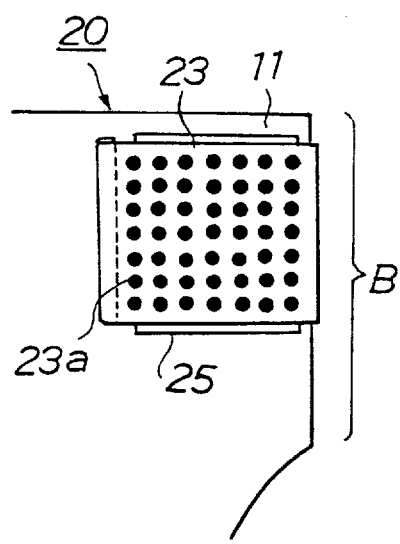
FIG. 4A is a front view showing a tape tab of a disposable diaper according to the second embodiment of the present invention.
Figure 4B:
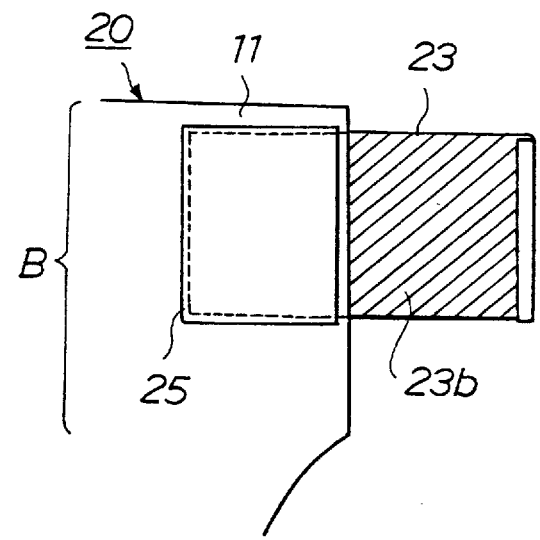
Figure 4C:
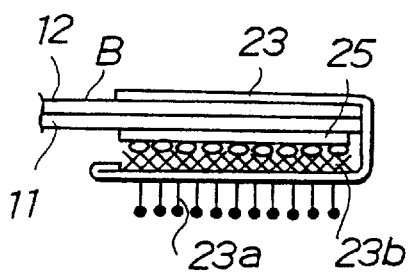
FIG. 4C is a side view showing the tape tab of the disposable diaper according to the second embodiment of the present invention.
Figure 4D:
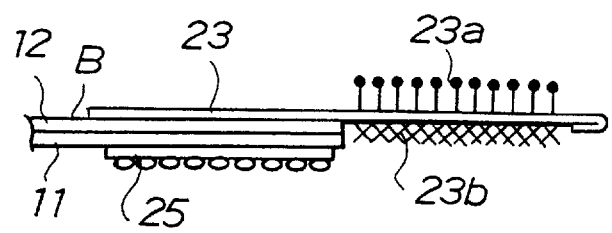

FIG. 4A is a front view showing tape tabs of a disposable diaper according to the second embodiment of the present invention, FIG. 4B is a side view showing a form of use of the tape tabs just prior to when the disposable diaper according to the second embodiment of the present invention is to be disposed of, FIG. 4C is a side view showing the tape tabs of the disposable diaper according to the second embodiment of the present invention, and FIG. 4D is a side view showing a form of use of the tape tabs just prior to when the disposable diaper according to the second embodiment of the present invention is to be disposed of.

In the disposable diaper 20 of this second embodiment, as shown in FIGS. 4A, 4B, 4C and 4D, the projection members 23a of the mechanical fastener forming engaging portions are secured to a generally entire area of the extended portion of the tape tab 23 from the rear waist body portion B of the surface on the backsheet 12, whereas an adhesive agent is applied to the generally entire area of the surface on the side opposite thereby forming an adhesive portion 23b. A peeling sheet 25 serving as the associated portion is secured to the topsheet 11 side of each of the opposite lateral side portions of the rear waist body portion B, and a peeling agent is applied to the surface of this peeling sheet 25. There is no provision of an associated portion on the tape tab 23 as in the first embodiment of the present invention. Then, the tape tab 23 is bent back at an area in the vicinity of a side edge of the rear waist body portion B, and the generally entire area of the extended portion from the rear waist body portion B of the tape tab 23 is attached to the peeling sheet 25, so that the projection members 23a are arranged on the topsheet 11 side. The remaining construction is about the same as the above-mentioned first embodiment.

The disposable diaper 20 according to this second embodiment is worn by the same operation as in the first embodiment. Further, through the same operation as in the first embodiment, the adhesive portion 23b is exposed for maintaining the disposable form.

The same functions and effects as the first embodiment can also be obtained by the disposable diaper 20 of this second embodiment.

According to the disposable diaper 20 of this second embodiment, since the opposite lateral side portions of the rear waist body portion B are retained by the counterpart portion 14 through the tape tab 23, the rear waist body portion B can more positively be engaged with and retained by the front waist body portion A.

Further, according to the disposable diaper 20 of this second embodiment, since the opposite lateral side portions of the rear waist body portion B are fixedly attached to the backsheet 12 through the peeling sheet 25 in the disposable form, the disposable form can more easily and reliably be maintained.

The present invention is not limited to the above-mentioned first and second embodiments but changes can appropriately be made without departing from the spirit and scope of the present invention.

For example, the associated portion 13c and the peeling sheet 25 may be formed by spraying an adhesive agent, instead of applying the adhesive agent, to form a thin film.

The peeling agent of the associated portion 13c and the peeling sheet 25 are not particularly limited as long as they can peelably be attached. For example, those areas which do not function as an adhesive agent after the adhesive portions 13b and 23b are peeled off, may be used.

The peeling force between the adhesive portion 13b and the associated portion 13c, or between the adhesive portion 23b and the peeling sheet 25 is not limited to 100 g/25 mm width. However, the peeling force is preferably from 25 to 500 g/25 mm width so that the adhesive portion 13b and the associated portion 13c, or the adhesive portion 23 and the peeling sheet 25 are not peeled off when the disposable diaper is in use and the peeling-off can easily be made when the disposable form is created.

Furthermore, where a non-woven fabric is disposed on the front waist body portion A which can serve as the counterpart portion 14, there is no need of providing particularly the recess member of a mechanical fastener.

Moreover, it is possible that the engaging portions are formed of the recess members of the mechanical fastener and the counterpart portion 114 is formed of the projection member of the mechanical fastener.

Also, it goes without saying that a specific configuration, dimension, etc. of each component member is not limited in dimension or the like to the above-mentioned embodiments.

The third embodiment of a disposable diaper of the present invention will be concretely described with reference to the accompanying drawings.

Figure 5:
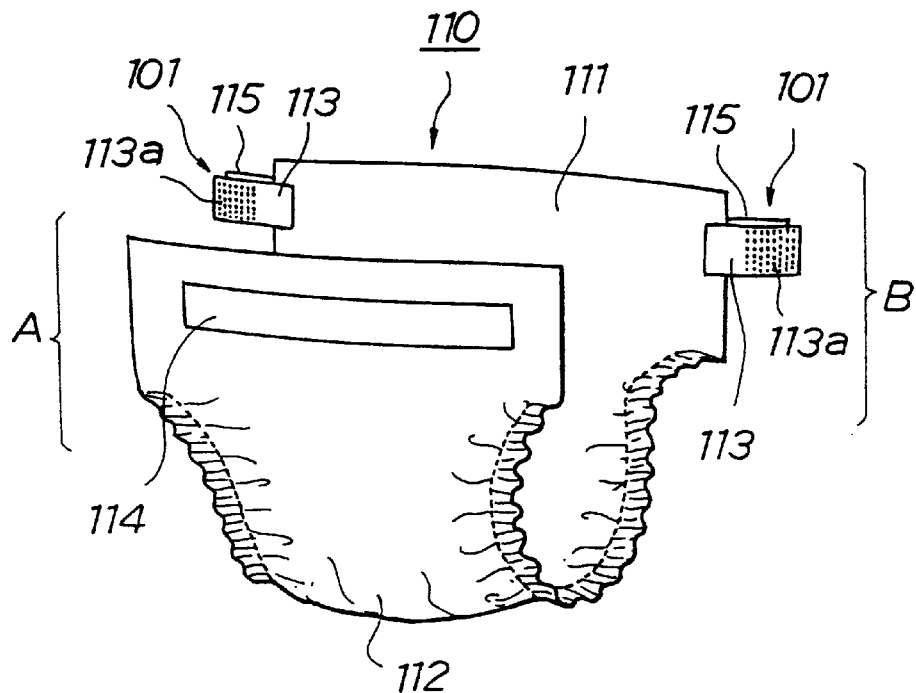
FIG. 5 is a perspective view showing a disposable diaper according to the third embodiment of the present invention.
Figure 6A:
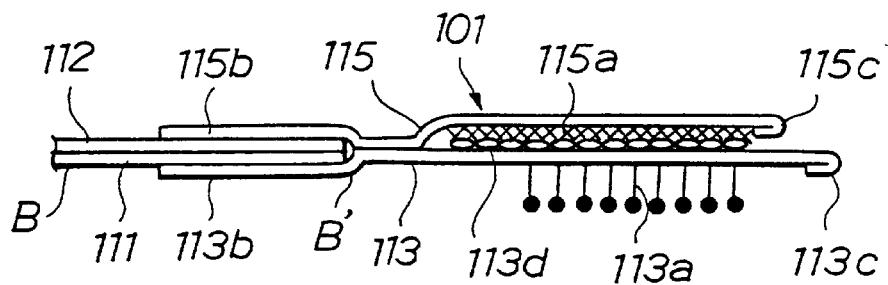
FIG. 6A is a side view showing a tape tab of the disposable diaper of FIG. 5.
Figure 6B:
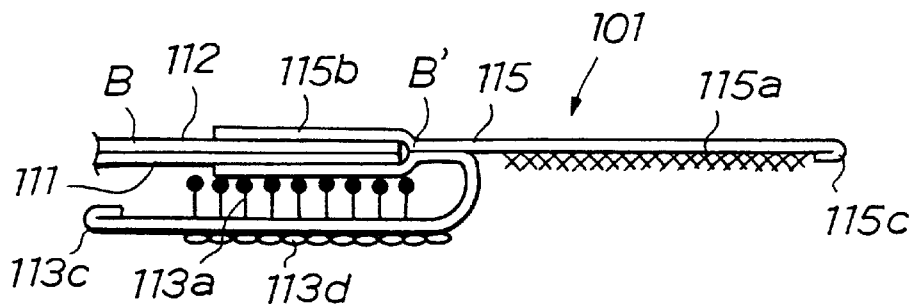

FIG. 5 is a perspective view showing a disposable diaper according to the third embodiment of the present invention, FIG. 6A is a side view showing a tape tab of the disposable diaper of FIG. 5, and FIG. 6B is a side view showing a form of use of the tape tab of the disposable diaper of FIG. 5 prior to when the diaper is to be disposed of. As shown in FIG. 5, a disposable diaper 110 according to this third embodiment includes a liquid permeable topsheet 111, a liquid impermeable backsheet 112, and an absorbent member (not seen) interposed between the topsheet 111 and the backsheet 112. A front waist body portion A, which is located on the stomach side of the diaper wearer when the diaper is worn, and a rear waist body portion B, which is located on the back side of the diaper wearer when the diaper is worn, are formed on the diaper 110. Tape tabs 101 are connected at opposite lateral side portions of the rear waist body portion B. The tape tab 101 is provided on a surface on the topsheet side 111 with a projection member 113a of a mechanical fastener to thereby form an engaging portion. The front waist body portion A is provided with a counterpart portion 114 comprising a recess member of the mechanical fastener. Constructions thereof are known per se.

As shown in FIGS. 6A and 6B, in the disposable diaper 110 according to this third embodiment, the tape tab 101 includes an adhesive tape portion 115 and an adhesive portion 115a which is formed by applying an adhesive agent thereto and a retaining tape portion 113.

This embodiment will now be described in de-tail. The tape tab 101 comprises a retaining tape portion 113 having the engaging portion formed by the projection members 113a of the mechanical fastener, and an adhesive tape portion 115 having the adhesive portion 115a. The retaining tape portion 113 is connected with the opposite lateral side portions of the rear waist body portion B. The projection members 113a of the mechanical fastener are provided on a surface on the topsheet 111 side of the retaining tape portion 113, thereby forming the engaging portion. The retaining tape portion 113 is provided, on its backsheet 112 side surface, with an associated portion 113d capable of peelably attaching the adhesive portion 115a thereto without losing adhesive properties of the adhesive agent. The adhesive tape portion 115 is secured at its basal end portion 115b to an upper surface of the backsheet 112 of the rear waist body portion B. The adhesive portion 115a is provided at that location on the adhesive tape portion 115 which faces the surface opposite the engaging portion of the retaining tape portion 113. The adhesive portion 115a of the adhesive tape portion 115 attaches to the associated portion 113d.

This embodiment will be now described in more detail. The basal end portion 113b of the retaining tape portion 113 is secured to the topsheet 111 of the rear waist body portion B, and a distal end of the retaining tape portion 113 is bent back in overlapped relation, thereby forming a handle portion 113c. This projection members 113a are provided on the distal end side of the retaining tape portion 113. The retaining tape portion 113 is provided, on its opposite surface with respect to the projection members 113a, with an associated portion 113d which is subjected to peeling agent treatment.

The basal end portion 115b of the adhesive tape portion 115 is secured to the backsheet 112 of the rear waist body portion B, and an immediate distal end side of the basal end portion 115b is secured to the retaining tape portion 113. The distal end is bent back in overlapped relation, thereby forming a handle portion 115c. A generally entire surface of the adhesive tape portion 115, which faces the retaining tape portion 113, serves as the adhesive portion 115a between its securing portion with respect to the retaining tape portion 113 and the handle portion 115c. The adhesive tape portion 115 is attached to the associated portion 113d of the retaining tape portion 113 through the adhesive portion 115a.

The material of the retaining tape portion 113 and the adhesive tape portion 115 may be the same as that of the conventional tape tab as in the first embodiment.

The projection members 113a of the mechanical fastener may be the same as that of the first embodiment.

The associated portion 113d and the adhesive portion 115a are formed by the same adhesive agent or peeling agent as in the first embodiment and in the same manner as in the first embodiment.

A peeling force between the adhesive portion 115a and the associated portion 113d is 100 g/25 mm width.

The peeling force between the adhesive portion 115a and the associated portion 113d is preferably from 25 to 500 g/25 mm width particularly about 100 g/25 mm. If the peeling force is smaller than 25 g/25 mm, there is a fear that the adhesive portion 115a and the associated portion 113d are peeled off in wear. If the peeling force is larger than 500 g/25 mm, the adhesive portion 115a is not readily peeled off in use.

It should be noted that the peeling force between the adhesive portion and the associated portion 113d is defined in the same manner as in the first embodiment.

In the disposable diaper 110 thus constructed according to this third embodiment, before use, both the adhesive tape portion 115 and the retaining tape portion 113 are bent at a side edge portion B', as in FIGS. 6A and 6B of the rear waist body portion B, and the projection members 113a of the retaining tape portion 113 is in contact (not shown) at its surface with the topsheet 111 of the rear waist body portion B.

For wear, as shown in FIG. 6A, while allowing the adhesive tape portion 115 to attach to the retaining tape portion 113, the projection members 113a of the retaining tape portion 113 is brought to engage with and retained by the counterpart portion 114 of the front waist body portion A.

For disposal, as shown in FIG. 6B, the retaining tape portion 113 is peeled off the adhesive tape portion 115, and then the retaining tape portion 113 is bent back at its securing portion (side edge portion B' of the rear waist body portion B) with respect to the adhesive tape portion 115, so that the projection members 113a are brought into engagement with the topsheet 111 and the adhesive portion 115a of the adhesive tape portion 115 is exposed. Then, the disposable diaper 110 is rolled up from an edge portion of the stomach side A towards the rear waist body portion B with the topsheet 111 side facing inside, and in that state, the adhesive tape portion 115 is attached to the backsheet 112 through the adhesive portion 115a. By doing this, there can be obtained the same disposable form of the disposable diaper 110 as in the first embodiment shown in FIG. 3.

In this way, according to the disposable diaper 110 of this third embodiment, when the diaper 110 is in use, the rear waist body portion B can positively be secured to the front waist body portion A by the mechanical fastener of the projection members 113a of the retaining tape portion 113, and when the diaper 110 is to be disposed of, the disposable form of the disposable diaper 110 can be maintained by the adhesive tape portion 115.

Also, according to the disposable diaper 110 of this third embodiment, since the adhesive portion 115a is covered by the associated portion 113d which is formed on the retaining tape portion 113, the adhesive portion 115a does not get dirty when the diaper is in use and the disposable form of the disposable diaper 110 can positively be maintained when the diaper is to be disposed.

Moreover, according to the disposable diaper 110 of this third embodiment, since the adhesive portion 115a is covered with the associated portion 113d which is formed on the retaining tape portion 113, peelable paper, etc. which are required to be disposed of are not necessary for disposing the disposable diaper.

Also, according to the disposable diaper 110 of this third embodiment, since the adhesive portion 115a is formed on a large part of the surface of the adhesive tape portion 115 which extends from the rear waist body portion B, the adhesive tape portion 115 can easily and positively be retained by the backsheet 112, so that a disposable form of the disposable diaper can be secured.

The fourth embodiment of a disposable diaper according to the present invention will now be described. In this embodiment, identical members to those of the disposable diaper 110 according to the third embodiment as shown in FIGS. 5, 6A and 6B are denoted by identical reference numerals, and description thereof is omitted.

Figure 7:
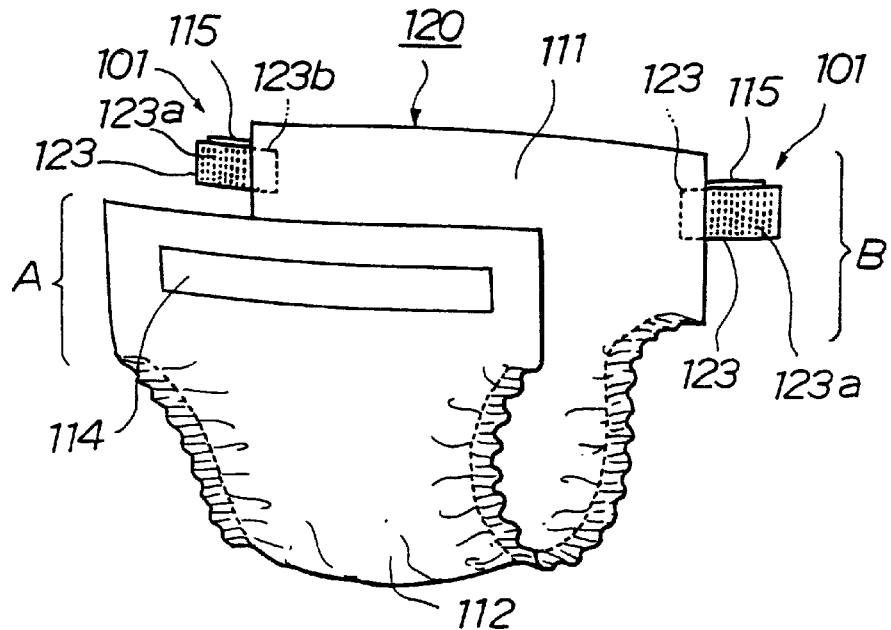
FIG. 7 is a perspective view showing a disposable diaper according to the fourth embodiment of the present invention.
Figure 8A:
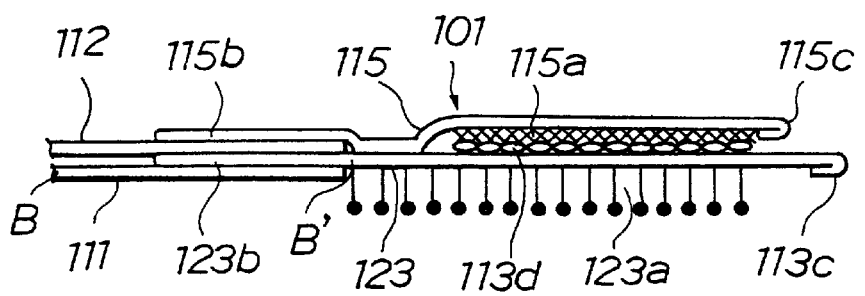
FIG. 8A is a side view showing a tape tab of the disposable diaper of FIG. 7.
Figure 8B:
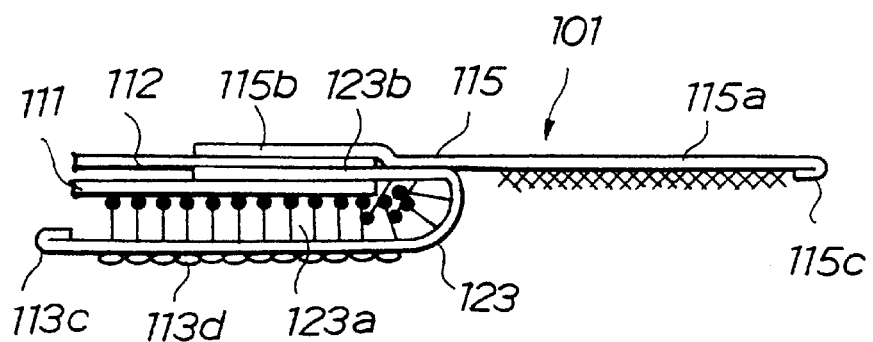

FIG. 7 is a perspective view of a disposable diaper according to the fourth embodiment of the present invention, FIG. 8A is a side view showing a tape tab of the disposable diaper of FIG. 7, and FIG. 8B is a side view showing a form of use of the tape tab when the disposable diaper of FIG. 7 is disposed.

In a disposable diaper 120 according to this fourth embodiment, as shown in FIGS. 7, 8A and 8B, retaining tape portions 123 are fixedly retained at their basal end portions 123b between the topsheet 111 and the backsheet 112 in the rear waist body portion B. Engaging portions 123a comprising projection members of the mechanical fastener are arranged from areas in the vicinity of distal ends thereof to opposite lateral side portions of the rear waist body portion B.

Construction of the remaining portions are the same as the third embodiment.

The retaining tape portions 123 may use the same material as the retaining tape portions 113 of the third embodiment. Similarly, the projection members 123a of the retaining tape portions 123 may be the same projection members 113a of the mechanical fasteners of the third embodiment.

The disposable diaper 120 according to this fourth embodiment is worn through the same operation as in the third embodiment. Also, the disposable form of FIG. 8B can be obtained through the same operation as in the third embodiment.

The disposable diaper 120 according to this fourth embodiment can also exhibit the same actions and effects as the disposable diaper 110 of the third embodiment.

Furthermore, according to the disposable diaper 120 of this fourth embodiment, since the projection members 123a are formed on almost the entire area of that portion of one surface of the retaining tape portion 123 which extends from the rear waist body portion B, the disposable form can firmly and positively be maintained by the counterpart portion 114.

Moreover, since the retaining tape portions 123 are retained between the topsheet 111 and the backsheet 112, and the topsheet 111 is exposed at the opposite lateral sides of the rear waist body portion, both the adhesive tape portions 115 and the retaining tape portions 123 can be retained in the fixedly bent form by engaging the projection members 123a to the topsheet 111 at the opposite lateral sides before use. Accordingly, the diaper is easier to handle, and the projection members 123a are kept from being exposed to the outside and from being exposed to the outside and from being weakened in their engaging force.

The fifth embodiment of a disposable diaper according to the present invention will now be described. In this fifth embodiment, the same component members as the disposable diaper 110 of the third embodiment of FIGS. 5, 6A and 6B are denoted by the same reference numerals and description thereof is omitted.

Figure 9A:
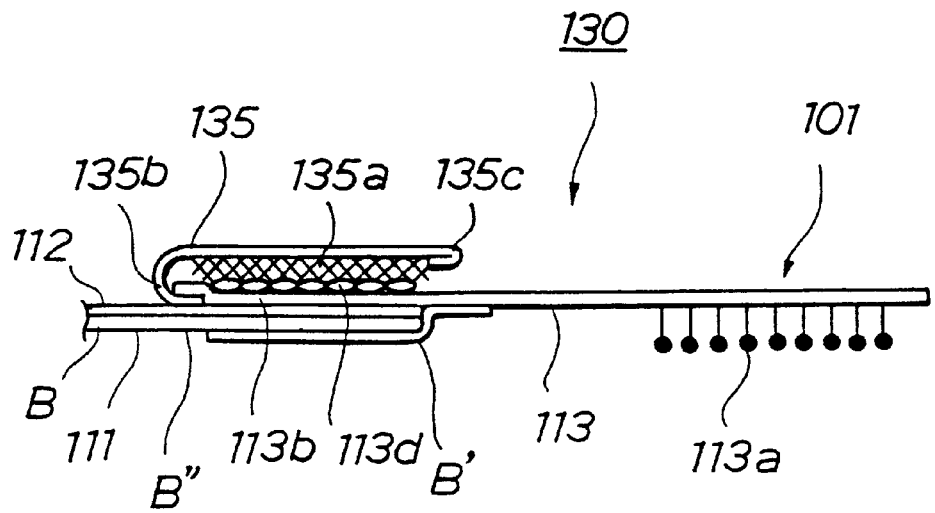
FIG. 9A is a side view showing a tape tab of a disposable diaper according to the fifth embodiment of the present invention.
Figure 9B:
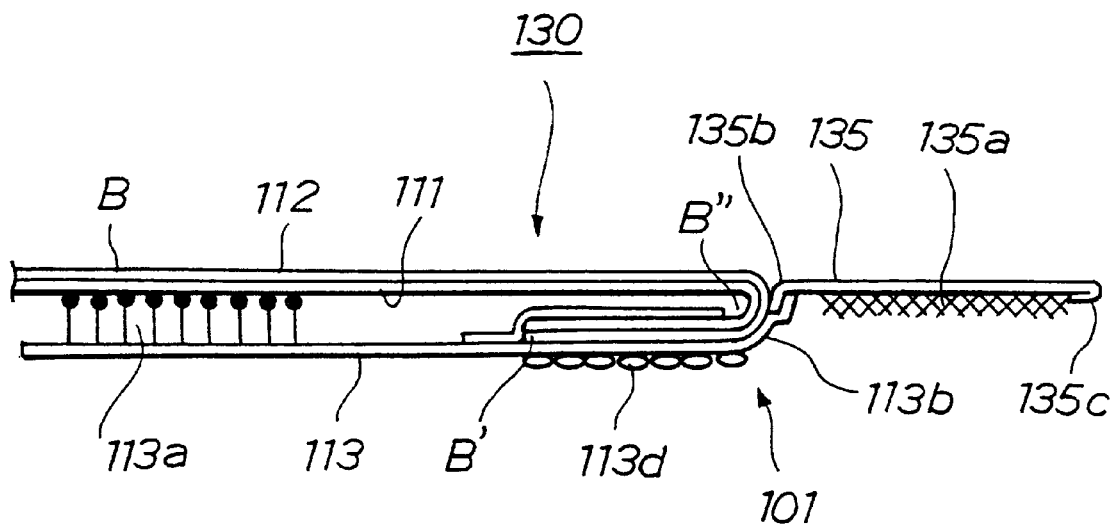

FIG. 9A is a side view showing a tape tab of a disposable diaper according to the fifth embodiment of the present invention, and FIG. 9B is a side view showing a form of use of the tape tab when the disposable diaper according to the fifth embodiment of the present invention is disposed.

In a disposable diaper 130 according to this embodiment, as shown in FIG. 9A, a retaining tape portion 113 is secured at its basal end portion 113b to a surface of at least the rear waist body portion B, whereas an adhesive portion 135a is provided at a location facing with the basal end portion 113b of the retaining tape portion 113 on an adhesive tape portion 135.

This fifth embodiment will now be described in detail. The basal end portion 113b of the retaining tape portion 113 is secured to the backsheet 112 side of the rear waist body portion B, and the same associated portion 113d as the third embodiment is provided on the basal end portion 113b.

The basal end portion 135b of the adhesive tape portion 135 is connected with the basal end portion 113b of the retaining tape portion 113, and the adhesive tape portion 135 is bent back at the basal end portion 135b. The adhesive portion 135a is provided at a location facing with the associated portion 113d, and the adhesive tape portion 135 is attached to the associated portion 113d of the retaining tape portion 113 through the adhesive portion 135a. The same handle 135c as the third embodiment is formed on a distal end of the adhesive tape portion 135. This handle portion 135c is faced with the distal end side of the basal end portion of the retaining tape portion 113.

A construction of the remaining portion is the same as the third embodiment.

The adhesive tape portions 135 may use the same material as the adhesive tape portions 115 of the third embodiment. Similarly, the adhesive portions 135a of the adhesive tape portions 135 may be the same as the adhesive portions 115a of the third embodiment.

In the disposable diaper 130 according to this embodiment, before use, the retaining tape portion 113 is bent at a side edge portion B' of the rear waist body portion B, and the projection members 113a of the retaining tape portion 113 is in contact (not shown) at its surface with the topsheet 111 of the rear waist body portion B.

For use in wear, as shown in FIG. 9A, the retaining tape portion 113 is developed, and the projection members 113a of the retaining tape portion 113 is brought into engagement with and retained by the counterpart portion 114.

For disposal, as shown in FIG. 9B, the retaining tape portion 113 is peeled off the adhesive tape portion 135, and then the adhesive portion 135a is exposed. Further, the rear waist body portion B of the disposable diaper 130 is bent back at a certain location B" of the connecting portion between the retaining tape portion 113 and the adhesive tape portion 135, and then the projection members 113a of the retaining tape portion 113 is engaged with the topsheet 111. At the same time, the adhesive portion 135a of the adhesive tape portion 135 is arranged on the topsheet 111 side of the disposable diaper 130. Then, a disposable form can be obtained in the same manner as in the third embodiment.

The present invention should not be limited to the above-mentioned third to fifth embodiments. Specific shapes, dimensions, etc. of various component members can appropriately be changed without departing from the spirit of the present invention. Locations of arrangement of the projection members at the surface of the retaining tape portions on the topsheet side, etc. can be mutually exchanged in the above-mentioned embodiments.

For example, in the third embodiment (FIGS. 5, 6 and 6B), and in the fifth embodiment (FIGS. 9A and 9B), it is possible, as in the fourth embodiment of FIGS. 7, 8A and 8B, that the projection members 113a are arranged from the areas in the vicinity of the distal ends of the retaining tape portions 113 to the edge ends of the opposite lateral side portions of the rear waist body portion B, and the basal end portions 113b of the retaining tape portions 113 are held between the topsheet 111 and the backsheet 112 and secured to the rear waist body portion B.

In the third to fifth embodiments, the projection members 113a, 123a of the mechanical fastener forming the engaging portions of the retaining tape portions 113, 123 may be integral with the retaining tape portions 113, 123.

In the third to fifth embodiments, the peeling agent of the associated portions 113d may be selected from those which are capable of peelably attaching the adhesive portions 113d thereto without losing adhesive properties of the adhesive agent. The peeling agent may also be selected from those which do not function as an adhesive agent after the adhesive portions 113d are peeled off.

In the third to fifth embodiments, in case where non-woven fabric is arranged on the front waist body portion A, it is not especially required to pro-vide the recess members of the mechanical fastener because the non-woven fabric functions as the counter-part portions 114.

In the third to fifth embodiments, it is possible that the engaging portions are formed of the recess members of the mechanical fastener and the counterpart portion 114 is formed of the projection member of the mechanical fastener.

In the third to fifth embodiments, the retaining tape portions 113, 123 may be integral with the adhesive tape portions 115, 135.

Figure 10:
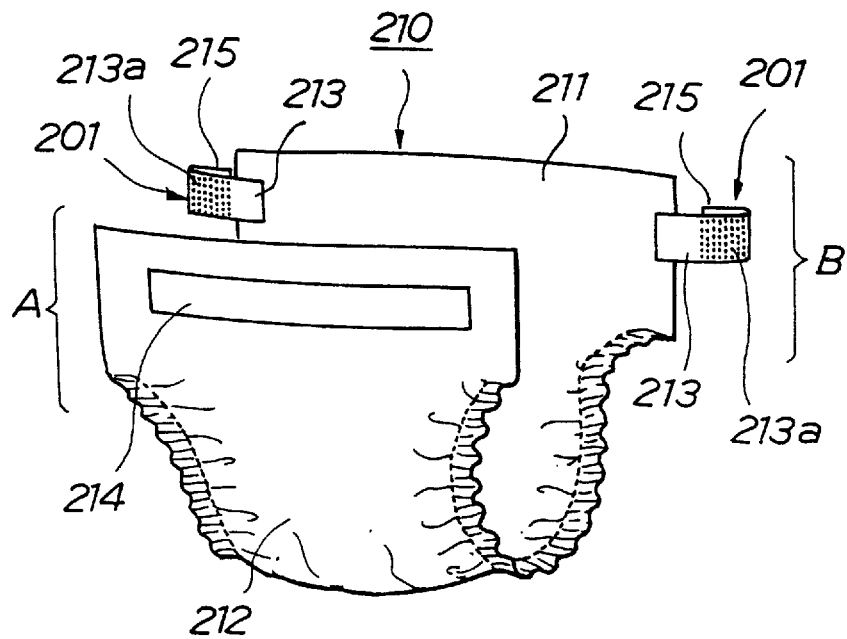
FIG. 10 is a perspective view showing a disposable diaper according to the sixth embodiment of the present invention.

The sixth embodiment of a disposable diaper according to the present invention will be specifically described with reference to the accompanying drawings. FIG. 10 is a perspective view showing a disposable diaper according to the sixth embodiment of the present invention, FIG. 11A is a side view showing a tape tab of the disposable diaper of FIG. 10, and Fig. 11B is a side view showing a form of use of the tape tab prior to when the disposable diaper of FIG. 10 is to be disposed of.

As shown in FIG. 10, a disposable diaper 210 according to this sixth embodiment includes a liquid permeable topsheet 211, a liquid impermeable backsheet 212, and an absorbent member (not shown) interposed between the topsheet 211 and the backsheet 212. In this diaper 210, there are provided a front waist body portion A which is located on the stomach side of the diaper wearer when the diaper is worn, and a rear waist body portion B which is located on the back side of the diaper wearer when the diaper is worn. Tape tabs 201 are connected at opposite lateral side portions of the rear waist body portion B. Each of the tape tabs 201 is provided with a projection member 213a of a mechanical fastener to thereby form an engaging portion. On the front waist body portion A, there is a provision of a counterpart portion 214. The projection member 213a of the mechanical fastener is engaged with and retained by the counterpart portion 214. These constructions are the same as those of the known techniques.

Figure 11A:
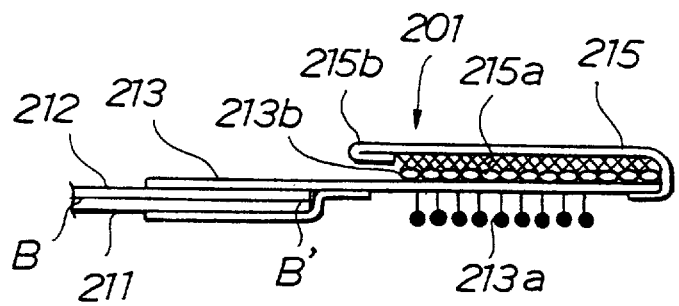
FIG. 11A is a side view showing a tape tab of the disposable diaper of FIG. 10.
Figure 11B:
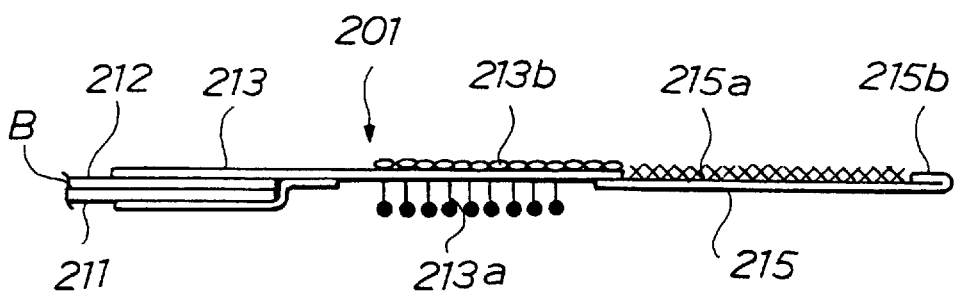
Figure 12A:
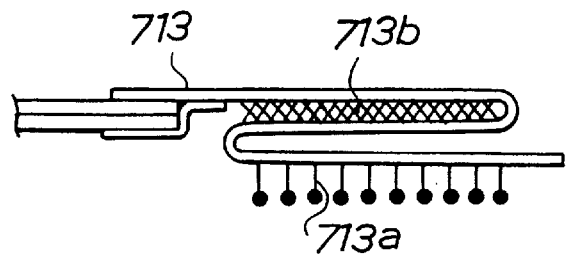
FIG. 12A is a side view showing one example of a tape tab of a conventional disposable diaper.
Figure 12B:
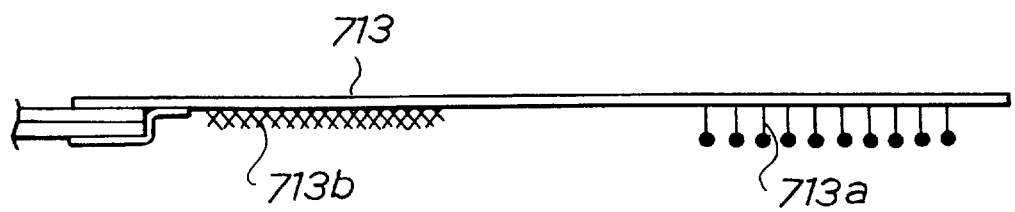
Figure 13:
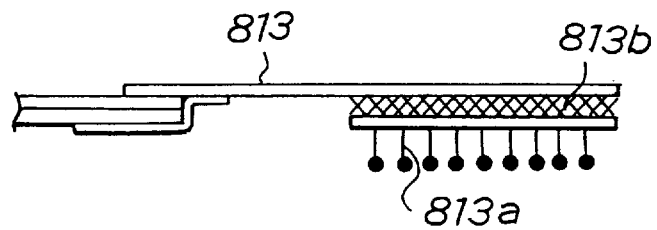
FIG. 13 is a side view showing another example of a tape tab of the conventional disposable diaper.
Figure 14:
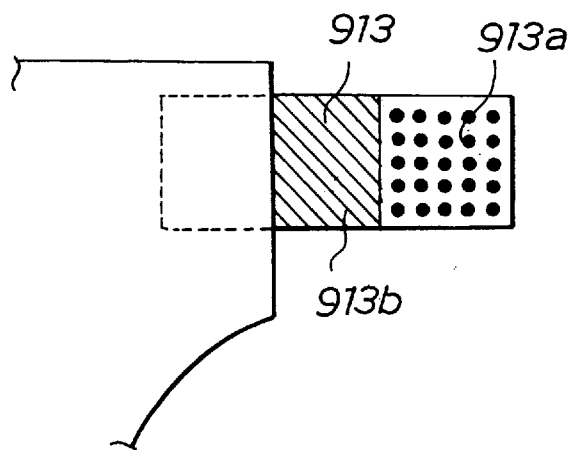
FIG. 14 is a front view showing still another example of a tape tab of the conventional disposable diaper.

In the disposable diaper 210 of this sixth embodiment, as shown in Fig. 11A, the tape tab 201 includes an adhesive portion 215a which is formed by applying an adhesive agent thereto. The adhesive portion 215a is disposed on an opposite surface side with respect to a surface of the tape tab 201 where the projection member 213a of the mechanical fastener is provided.

The tape tab 201 comprises a retaining tape portion 213 having the projection member 213a of the mechanical fastener, and an adhesive tape portion 215 having the adhesive portion 215a. The retaining tape portions 213 are connected with the opposite lateral side portions of the rear waist body portion B. The projection member 213a of the mechanical fastener is provided on the topsheet 211 side of the retaining tape portion 213. The retaining tape portion 213 is provided, on a back side of its surface where the projection member 213a of the mechanical fastener is provided, with an associated portion 213b which is capable of peelably attaching the adhesive portion 215a thereto without losing properties of the adhesive agent. The adhesive tape portion 215 is connected with a distal end portion of the retaining tape portion 213 to pro-vide a connecting portion including the distal end portion of the retaining tape portion 213 and a distal end portion of the adhesive tape portion 215. The adhesive portion 215a is located on an opposite surface side of the adhesive tape portion 215 with respect to a surface where the projection member 213a of the mechanical fastener of the retaining tape portion 213 is disposed. The connecting portion is bent back, and the adhesive portion 215a is attached to the associated portion 213b.

This embodiment will now be described in de-tail. One end (basal end portions) of the retaining tape portions 213 are secured to the opposite lateral side portions of the rear waist body portion B, respectively. The projection member 213a of the mechanical fastener is secured to that part of the surface of the retaining tape portion 213 on the topsheet 211 side which extends from the rear waist body portion B. A generally entire surface of that part of the opposite surface with respect to a surface where the projection member 213a is provided and extending from the rear waist body portion B is subjected to peeling treatment so that the associated portion 213b is formed.

A distal end portion of the adhesive tape portion 215 is bent back to form the handle portion 215b. An opposite surface (the same side surface with respect to the associated portion 213b of the retaining tape portion 213) with respect to the surface where the projection member 213a of the mechanical fastener of the retaining tape portion 213 is applied with an adhesive agent from the connecting portion between the retaining tape portion 213 and the adhesive tape portion 215 to the handle portion 215b, thereby forming the adhesive portion 215a.

A recess member of the mechanical fastener is secured to the front waist body portion A of the disposable diaper 210 according to this embodiment, thus forming the counterpart portion 214.

The material of the retaining tape portion 213 and the adhesive tape portion 215 may be the same as that of the conventional tape tab as in the first embodiment.

The projection member 213a of the mechanical fastener may be the same as that of the first embodiment.

The associated portion 213b and the adhesive portion 215a are formed by the same peeling agent or adhesive material as in the first embodiment and in the same manner as in the first embodiment.

It should be noted that this peeling force between the adhesive portion 215a and the associated portion 213b is defined in the same manner as in the first embodiment.

A peeling force between the adhesive portion 215a and the associated portion 213b is 100 g/25 mm width.

The peeling force between the adhesive portion 215a and the associated portion 213b is preferably from 25 to 500 g/25 mm width particularly about 100 g/25 mm. If the peeling force is smaller than 25 g/25 mm, there is a fear that the adhesive portion 215a and the associated portion 213b are peeled off in wear. If the peeling force is larger than 500 g/25 mm, the adhesive portion 215a is not readily peeled off in use.

In the disposable diaper 210 thus constructed according to this embodiment, before use, as shown in Fig. 11A, the retaining tape portion 213 having its adhesive portion 215a attached to the associated portion 213b of the retaining tape portion 213 is bent back at a side edge portion B' of the rear waist body portion B and the projection member 213a of the retaining tape portion 213 is in contact (not shown) at its surface with the topsheet 211 of the rear waist body portion B.

For use, as shown in Fig. 11A, the adhesive portion 215a of the adhesive tape portion 215 is attached to the associated portion 213b of the retaining tape portion 213 and in that state, the projection member 213a of the retaining tape portion 213 is brought into engagement with and retained by the counterpart portion 214.

For disposal or the like, as shown in FIG. 11B, the handle portion 215b of the adhesive tape portion 215 is pulled to peel the adhesive portion 215a off the associated portion 213b of the retaining tape portion 213. Then, the disposable diaper 210 is rolled up with the backsheet 212 side facing outside, so that a disposal shape can be created utilizing the exposed adhesive portion 215a.

In this way, according to the disposable diaper 210 of this embodiment, since the adhesive portion 215a is covered with the associated portion 213b and there-fore, not utilized when the diaper is worn by the diaper wearer, it can fully exhibit the advantages of the mechanical fastener and thus the retaining tape portion 213 can positively be retained by the counter-part portion 214.

Also, according to the disposable diaper 210 of this embodiment, since the adhesive portion 215a is covered with the associated portion 213b formed on the retaining tape portion 213, such things as peelable paper, etc. which are required to be disposed are not generated when the adhesive portion 215a is exposed for disposing the disposing the disposable diaper.

Moreover, according to the disposable diaper 210 of this embodiment, since the adhesive portion 215a is formed generally over an entire surface of one surface of the adhesive tape portion 215, a disposable form of the disposable diaper 210 can easily and positively be maintained by this adhesive tape portion 215.

The present invention should not be limited to the above-mentioned embodiments. The embodiments described can appropriately be changed without departing from the spirit of the invention.

For example, the retaining tape portion 213 and the adhesive tape portion 215 may be integrally formed.

The peeling agent of the associated portions 213d may be selected from those which are capable of peelably attaching the adhesive portions thereto with-out losing adhesive properties of the adhesive agent. The peeling agent may also be selected from those which do not function as an adhesive agent after the adhesive portions 215a are peeled off.

Furthermore, where a non-woven fabric is arranged on the front waist body portion A, it is not especially required to provide the recess members of the mechanical fastener because the non-woven fabric functions as the counterpart portions 214.

Moreover, it is possible that the engaging portions are formed of the recess members of the mechanical fastener and the counterpart portion 214 is formed of the projection member of the mechanical fastener.

It goes without saying that specific shapes, dimensions, etc. of the various component parts are not limited to the above-mentioned embodiments.

What is claimed is:

1. A disposable diaper including a liquid permeable topsheet, a liquid impermeable backsheet, and an absorbent member interposed therebetween, the disposable diaper being provided with a front waist body portion which is located on the stomach side of a diaper wearer when the wearer puts on the diaper and a rear waist body portion which is located on the back side of the wearer;

tape tabs being connected at opposite lateral sides of the rear waist body portion, respectively;

a projection member or a recess member of a mechanical fastener being disposed on each tape tab to thereby form an engaging portion;

a counterpart portion being disposed on the backsheet side of the front waist body portion for allowing the projection member or the recess member to be engaged with or be retained by the counterpart portion;

an adhesive portion being disposed on each tape tab, said adhesive portion being formed by applying an adhesive agent to each tape tab; the adhesive portion being disposed on a surface of each tape tab opposite to where each projection member or each recess member of the mechanical fastener is disposed, said adhesive agent being made from any one of rubber adhesive agents, silicone-contained rubber adhesive agents, acrylic adhesive agents, silicone-contained acrylic adhesive agents, and silicone adhesive agents; and an associated portion includes a self-adhesive agent peelably attaching and covering each adhesive portion without losing adhesive properties of the adhesive agent when attached to each adhesive portion, each associated portion substantially reducing contamination of each adhesive portion prior to separation with each adhesive portion, the associated portion being an adhesive agent after separation from a respective adhesive portion, the adhesive portion and the associated portion being peelably attached together with a peeling force of generally 25 to 500 g/25 mm width, said associated portion substantially eliminating peelable sheets which cover said adhesive portion, said associated portion being a self-adhesive peeling agent selected from the group consisting of silicone resins, fluorine resins, and octadecyl isocyanate, when the disposable diaper is formed into a shape for disposal where the diaper is rolled up with the backsheet side facing outwardly, the tape tabs maintain the disposal shape of the diaper by the adhesive portions attaching to the liquid permeable backsheet.

2. The disposable diaper according to claim 1, wherein each projection member or each recess member of the mechanical fastener is disposed on the backsheet side of each of the tape tabs, said adhesive portion being disposed at a free end portion of a surface of each tape tab located on a side opposite a surface of a respective tape tab where each projection member or each recess member of the mechanical fastener is disposed, said associated portion being disposed where the adhesive portion does not exist, each of the tape tabs being in at least one of a folded and an extended condition, and each of said tape tabs being bent back in the folded condition such that the adhesive portion and the associated portion are attached together, and such that each projection member or each recess member projects in a topsheet side direction.

3. The disposable diaper according to claim 1, wherein each projection member or each recess member of the mechanical fastener is disposed on the backsheet side of each of the tape tabs, the adhesive portion is disposed on a surface of each tape tab which is located on the side opposite to where each projection member or each recess member of the mechanical fastener is disposed, the associated portion of each adhesive portion is disposed on the topsheet side on respective opposite lateral sides of the rear waist portion, each of the tape tabs being in at least one of a folded condition and an extended condition, said tape tabs being bent back at areas adjacent to side edges of the rear waist body portion in the folded condition such that the adhesive portion of each tape tab is attached to a respective associated portion of the rear waist body portion, and each projection member or each recess member of the mechanical fastener projects in a topsheet side direction.

4. The disposable diaper according to claim 1, wherein each of the tape tabs comprises a retaining tape portion, an adhesive tape portion having the adhesive portion, each retaining tape portion being connected to an opposite lateral side portion of the rear waist body portion, a surface of the topsheet side of each retaining tape portion being provided with each projection member or each recess member of the mechanical fastener, and a surface of the backsheet side of each retaining tape portion being provided with each associated portion, and each adhesive portion of each adhesive tape portion being attached to a respective associated portion.

5. The disposable diaper according to claim 4, wherein the adhesive tape portion is secured at a basal end portion thereof to a surface at the rear waist body position, and each adhesive portion is disposed at a respective adhesive tape portion which faces a surface of the retaining tape portion opposite to a surface where each projection member or each recess member is disposed.

6. The disposable diaper according to claim 4, wherein the retaining tape portion is secured at a basal end portion thereof to a surface of at least the rear waist body portion, and each adhesive portion is disposed at a respective adhesive tape portion which faces a basal end portion of the retaining tape portion.

7. The disposable diaper according to claim 4, wherein each projection member or each recess member of the mechanical fastener is disposed at a distal end of the retaining tape portion extending to a side edge of the rear waist body portion.

8. The disposable diaper according to claim 1, wherein each of the tape tabs comprises a retaining tape portion having each projection member or each recess member of the mechanical fastener, an adhesive tape portion having a respective adhesive portion, each retaining tape portion is connected at an opposite lateral side portion of the rear waist body portion, each projection member or each recess member of the mechanical fastener being disposed on a topsheet side of the retaining tape portion, the adhesive tape portion being connected at a distal end portion of the retaining tape portion to provide a connecting portion including the distal end portion of the retaining tape portion and a distal end portion of the adhesive tape portion, each adhesive portion provided on the adhesive tape portion is disposed on a surface opposite to a surface of the retaining tape portion where each projection member or each recess member of the mechanical fastener is disposed, each retaining tape portion being provided with an associated portion on a back side of a surface where each projection member or each recess member of the mechanical fastener is disposed, and when the connecting portion is in a bent, condition the adhesive portion is attached to the associated portion.

* * * * *